United States Patent
Liu et al.

(10) Patent No.: US 12,340,305 B2
(45) Date of Patent: Jun. 24, 2025

(54) TRAINING METHOD FOR AIR QUALITY PREDICTION MODEL, PREDICTION METHOD AND APPARATUS, DEVICE, PROGRAM, AND MEDIUM

(71) Applicant: BEIJING BAIDU NETCOM SCIENCE TECHNOLOGY CO., LTD., Beijing (CN)

(72) Inventors: Hao Liu, Beijing (CN); Jindong Han, Guangzhou (CN); Dejing Dou, Beijing (CN)

(73) Assignee: BEIJING BAIDU NETCOM SCIENCE TECHNOLOGY CO., LTD., Beijing (CN)

( * ) Notice: Subject to any disclaimer, the term of this patent is extended or adjusted under 35 U.S.C. 154(b) by 867 days.

(21) Appl. No.: 17/457,649

(22) Filed: Dec. 3, 2021

(65) Prior Publication Data

US 2022/0092418 A1    Mar. 24, 2022

(30) Foreign Application Priority Data

Dec. 22, 2020    (CN) .......................... 202011534216.8

(51) Int. Cl.
*G06N 3/08* (2023.01)
*G01N 33/00* (2006.01)
(Continued)

(52) U.S. Cl.
CPC .......... *G06N 3/08* (2013.01); *G01N 33/0062* (2013.01); *G06F 18/22* (2023.01); *G06F 18/29* (2023.01); *G06N 3/045* (2023.01)

(58) Field of Classification Search
CPC .......... G06N 3/08; G06N 3/045; G06F 18/22; G06F 18/29; G01N 33/0062
(Continued)

(56) References Cited

U.S. PATENT DOCUMENTS

2016/0125307 A1* 5/2016 Zheng ...................... G06N 3/08
706/20
2016/0318368 A1* 11/2016 Alger ............... G08G 1/096791
(Continued)

FOREIGN PATENT DOCUMENTS

AU    2019100364 A4    5/2019
CN    106485353 A    3/2017
(Continued)

OTHER PUBLICATIONS

Air Pollutant Concentration Prediction Based on GRU Method, by Zhou et al, 2019 (Year: 2019).*
(Continued)

*Primary Examiner* — Austin Hicks
(74) *Attorney, Agent, or Firm* — Hunton Andrews Kurth LLP

(57) ABSTRACT

Provided are a training method for an air quality prediction model, a prediction method and apparatus, a device, a program, and a medium. The method includes the steps described below. A target monitoring range is divided into a plurality of regions; the air quality prediction model is pre-trained by adopting a pre-training sample and a pre-training objective function, where the pre-training sample includes measurement values; and the pre-trained air quality prediction model is trained by adopting a formal training sample and a formal training objective function, where the formal training sample includes the measurement values. The air quality prediction model is configured to predict air quality of the plurality of regions according to spatial information, historical information and environmental information.

18 Claims, 3 Drawing Sheets

(51) Int. Cl.
  *G06F 18/20* (2023.01)
  *G06F 18/22* (2023.01)
  *G06N 3/045* (2023.01)

(58) Field of Classification Search
  USPC .......................................................... 706/15
  See application file for complete search history.

(56) References Cited

U.S. PATENT DOCUMENTS

| | | | |
|---|---|---|---|
| 2019/0250136 A1* | 8/2019 | Kim | G01N 33/0065 |
| 2020/0326195 A1* | 10/2020 | Gavranovic | G08G 1/0129 |

FOREIGN PATENT DOCUMENTS

| | | | |
|---|---|---|---|
| CN | 108875833 A | | 11/2018 |
| CN | 110567510 A | | 12/2019 |
| CN | 110598953 A | | 12/2019 |
| CN | 111461410 A | | 7/2020 |
| CN | 111754042 A | | 10/2020 |
| CN | 111814860 A | | 10/2020 |
| CN | 112085163 A | | 12/2020 |
| CN | 108052512 B | | 5/2021 |
| WO | 2018214060 A1 | | 11/2018 |
| WO | 2020009623 A1 | | 1/2020 |

OTHER PUBLICATIONS

Chakma et al., Image-Based Air Quality Analysis Using Deep Convolutional Neural Network, 2017 IEEE International Conference (5 pages).
Chinese First Search Report issued in corresponding Application No. 2020115342168 on Nov. 20, 2023 (6 pages).
Chinese Office Action issued in corresponding Application No. 2020115342168 on Nov. 22, 2023 (10 pages).
Chinese Supplemental Search Report issued in corresponding Application No. 2020115342168 on Jan. 14, 2024 (6 pages).
Wang et al., Air Quality Forecasting based on Gated Recurrent Long Short Term Memory Model in Internet of Things, IEEE Access, vol. 4, 2016 (11 pages).
Zhu et al., Forecasting model of environment air quality based on B-P. neural network, Computer Engineering and Applications, 2007, vol. 43, pp. 223-227.
Zhu et al., New Progress for Air Quality Forecasting Methods Based on Deep Learning, Environmental Monitoring in China, vol. 36, No. 3, Jun. 2020, 9 pages.

* cited by examiner

TRAINING METHOD FOR AIR QUALITY PREDICTION MODEL, PREDICTION METHOD AND APPARATUS, DEVICE, PROGRAM, AND MEDIUM

CROSS-REFERENCE TO RELATED APPLICATION(S)

This application claims priority to Chinese Patent Application No. 202011534216.8 filed Dec. 22, 2020, the disclosure of which is incorporated herein by reference in its entirety.

TECHNICAL FIELD

The present disclosure relates to the field of artificial intelligence, in particular, to deep learning technology and, specifically, to a training method for an air quality prediction model, a prediction method and apparatus, a device, a program, and a medium.

BACKGROUND

Rapid urbanization brings convenience to people's life, work, traffic and so on, but also inevitably causes frequent air pollution worldwide. If the air quality of various regions in a city can be accurately predicted in advance, potential loss caused by air pollution can be reduced or even prevented through pollution emission control and early intervention. However, due to high construction and maintenance costs, a city can only deploy a limited number of air quality monitoring stations which cannot cover every region of the city. Therefore, it is required to effectively predict future air quality of regions that are not covered by the monitoring stations.

The prediction of air quality depends on accurate pollution source information, or the prediction is relatively coarse-grained, the accuracy is low, so that the requirement of people for the fine-grained prediction of urban air quality cannot be satisfied.

SUMMARY

The present disclosure provides a training method for an air quality prediction model, a prediction method and apparatus, a device, a program, and a medium.

According to an aspect of the present disclosure, a training method for an air quality prediction model is provided. The method includes the steps described below.

A target monitoring range is divided into a plurality of regions, where the plurality of regions include measurement regions with air quality measurement values and prediction regions without the air quality measurement values, and the air quality measurement values in the measurement regions are acquired.

The air quality prediction model is pre-trained by adopting a pre-training sample and a pre-training objective function, where the pre-training sample includes the measurement values.

The pre-trained air quality prediction model is trained by adopting a formal training sample and a formal training objective function, where the formal training sample includes the measurement values.

The air quality prediction model is configured to predict air quality of the plurality of regions according to spatial information, historical information and environmental information.

According to another aspect of the present disclosure, an air quality prediction method is provided. The method includes the steps described below.

Air quality measurement values of at least one measurement region in a target monitoring range at least two occasions are acquired; where the target monitoring range is divided into a plurality of regions, and the plurality of regions include measurement regions with air quality measurement values and prediction regions without the air quality measurement values.

The air quality measurement values are input into an air quality prediction model, so as to predict an air quality value of the prediction regions at a future occasion after a current occasion.

The air quality prediction model is trained by the training method for an air quality prediction model of any embodiment of the present disclosure.

According to another aspect of the present disclosure, a training apparatus of an air quality prediction model is provided. The apparatus includes a region measurement value acquisition module, a model pre-training module and a model formal training module.

The region measurement value acquisition module is configured to divide a target monitoring range into a plurality of regions, where the plurality of regions include measurement regions with air quality measurement values and prediction regions without the air quality measurement values, and to acquire the air quality measurement values in the measurement regions.

The model pre-training module is configured to pre-train the air quality prediction model by adopting a pre-training sample and a pre-training objective function, where the pre-training sample includes the measurement values.

The model formal training module is configured to train the pre-trained air quality prediction model by adopting a formal training sample and a formal training objective function, where the formal training sample includes the measurement values.

The air quality prediction model is configured to predict air quality of the plurality of regions according to spatial information, historical information and environmental information.

According to another aspect of the present disclosure, an air quality prediction apparatus is provided. The apparatus includes a measurement value acquisition module and an air quality prediction module.

The measurement value acquisition module is configured to acquire air quality measurement values of at least one measurement region in a target monitoring range at least two occasions; where the target monitoring range is divided into a plurality of regions, and the plurality of regions include measurement regions with air quality measurement values and prediction regions without the air quality measurement values.

The air quality prediction module is configured to input the air quality measurement values into an air quality prediction model, so as to predict an air quality value of the prediction regions at a future occasion after a current occasion.

The air quality prediction model is trained by the training method for an air quality prediction model of any embodiment of the present disclosure.

According to another aspect of the present disclosure, an electronic device is provided, and the electronic device includes at least one processor and a memory.

The memory is communicatively connected to the at least one processor. The memory stores instructions executable by the at least one processor, and the instructions are executed by the at least one processor to cause the at least one processor to execute the training method for an air quality prediction model of any embodiment of the present disclosure or the air quality prediction method of any embodiment of the present disclosure.

According to another aspect of the present disclosure, a non-transitory computer-readable storage medium storing computer instructions is provided. The computer instructions are used for causing a computer to execute the training method for an air quality prediction model of any embodiment of the present disclosure or the air quality prediction method of any embodiment of the present disclosure.

According to another aspect of the present disclosure, a computer program product is provided. The computer program includes a computer program which, when executed by a processor, implements the training method for an air quality prediction model of any embodiment of the present disclosure or the air quality prediction method of any embodiment of the present disclosure.

According to the technology of the present disclosure, the problem of training an air quality prediction model for fine-grained regions is solved, the accuracy of a result of model training is improved, and the computing cost of model training is reduced.

It is to be understood that the content described in this part is neither intended to identify key or important features of the embodiments of the present disclosure nor intended to limit the scope of the present disclosure. Other features of the present disclosure are apparent from the description provided hereinafter.

BRIEF DESCRIPTION OF DRAWINGS

The drawings are intended to provide a better understanding of the present solution and not to limit the present disclosure.

DETAILED DESCRIPTION

Example embodiments of the present disclosure, including details of embodiments of the present disclosure, are described hereinafter in conjunction with the drawings to facilitate understanding. The example embodiments are illustrative only. Therefore, it is to be understood by those of ordinary skill in the art that various changes and modifications may be made to the embodiments described herein without departing from the scope and spirit of the present disclosure. Similarly, description of well-known functions and constructions is omitted hereinafter for clarity and conciseness.

Figure 1:
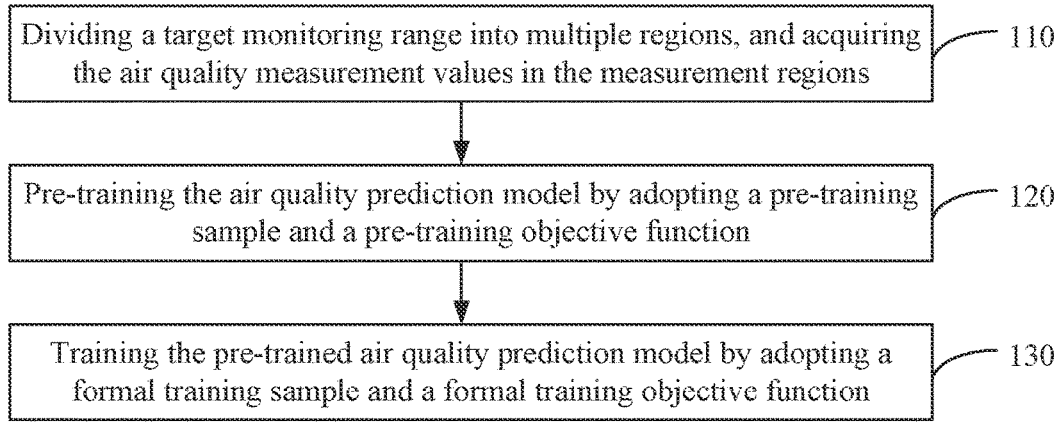
FIG. 1 is a flowchart of a training method for an air quality prediction model according to an embodiment of the present disclosure.

FIG. 1 is a flowchart of a training method for an air quality prediction model according to an embodiment of the present disclosure. The method is applicable to constructing and training an air quality prediction model.

At present, in order to perform air quality monitoring, air quality monitoring stations are generally disposed at some positions in a city, so as to monitor the air quality data in real time. The air quality data may be PM 2.5, PM 10 and other typical data characterizing the air quality. However, the coverage of air quality monitoring stations in a city is not very high, for example around 10%, so that the geographical range that air quality monitoring stations can measure is limited. According to the technical solution of the embodiment of the present disclosure, air quality measurement values provided by the limited number of air quality monitoring stations in a city may be configured as sample data to train the prediction model, so as to perform fine-grained prediction of the air quality of regions without air quality monitoring stations.

The training method for the model may be executed by a training apparatus of an air quality prediction model configured in a computing device. The apparatus may be implemented by software and/or hardware and configured in an electronic device having computing and storage capabilities. The method includes the steps described below.

In step S110, a target monitoring range is divided into multiple regions, and the air quality measurement values in the measurement regions are acquired, where the multiple regions include measurement regions with air quality measurement values and prediction regions without the air quality measurement values.

The target monitoring range is the target prediction range of the air quality prediction model, the model is trained based on sample data in the target monitoring range, and the trained model is also used for predicting the air quality of each region in the target monitoring range. The target monitoring range may be, for example, a geographic range at a city level.

The target monitoring range is divided into multiple non-overlapped regions. The shape and range of each region may be the same or different. The region division may be based on actual requirements. That is, the target prediction range may be divided into multiple regions in units of road sections or streets. A city as the target monitoring range is taken as an example, the city may be divided according to streets or towns of administrative regions, and each street may be configured as a region. The regions divided according to road sections or streets are more in line with air quality control goals. For example, for road sections or streets with poor air quality, industrial and green facilities may be planned, or traffic flow may be controlled.

These regions include measurement regions and prediction regions. The measurement regions are regions provided with air quality monitoring stations, that is, regions that can obtain air quality measurement values. The prediction regions are regions that cannot obtain the air quality measurement values.

In the measurement regions, one or more air quality monitoring stations may exist, and the air quality measurement values of the measurement regions may be determined based on the monitoring values of the one or more air quality monitoring stations. Optionally, the air quality measurement values in the measurement regions are acquired through the steps described below.

Measurement values of one air quality monitoring station in the measurement regions are configured as the air quality measurement values of the measurement regions.

Alternatively, an average value of measurement values of multiple air quality monitoring stations in the measurement regions are calculated as the air quality measurement values of the measurement regions.

The air quality measurement values of the measurement regions are comprehensively determined by the measurement values of the multiple air quality monitoring stations, so that the air quality measurement values can be more accurate. A more concise calculation manner may be selected to reduce the computing cost.

In step S120, the air quality prediction model is pre-trained by adopting a pre-training sample and a pre-training objective function.

The air quality prediction model is configured to predict the air quality of the multiple regions according to spatial information, historical information and environmental information. The spatial information reflects the spatial influence between regions, the historical information reflects the historical air quality influence, and the environmental information reflects the environmental similarity between the regions. Thus, the air quality of the regions can be predicted according to the consideration of various factors.

In the embodiment of the present disclosure, a multi-view and multi-task air quality prediction framework is proposed, which learns and fuses the current air quality characterization of the prediction regions from different views.

Firstly, according to Tobler's first law of geography, spatially adjacent regions are more correlated than regions distant from each other, so that the air quality of the regions can be inferred based on the spatial adjacency relationships of the regions. That is, in the air quality prediction model, the spatial influence between regions is considered from the spatial view.

Secondly, the current air quality of the regions further depends on the air quality in a previous period, which should be taken into consideration during prediction. That is, the historical air quality influence is considered from the temporal view in the air quality prediction model.

Thirdly, two similar regions may have similar air quality. For example, if two regions are both adjacent to a greenbelt or an industrial region, the environmental context of the regions may further be considered as a factor for estimating the current air quality. The environmental context of the regions may be referred to as an environment semantic feature of the regions, and thus the environmental similarity of the regions is considered from the environmental view in the air quality prediction model.

The air quality characterization results from the spatial view, the temporal view and the environmental view of the regions are fused to predict the air quality of the regions. Due to the division of multiple regions and the need to correlate and predict the air quality from multiple views, the scale of the model is relatively large and the computational cost of training is relatively high. In order to improve the training efficiency, the embodiment of the present disclosure adopts a pre-training manner. The training sample and objective functions used in the pre-training are different from the training sample and objective functions of formal training.

Since the air quality prediction model of the embodiment of the present disclosure constructs the influence factors of the air quality of the regions from multiple views, the pre-training may be firstly performed from any one of the spatial view, the temporal view and the environmental view.

Preferably, the pre-training is performed on the spatial influence relationships of the regions from the spatial view. Since the air quality influence from the temporal view also needs to be predicted based on air quality basic data of the regions, and the influence from the environmental view may be excluded, the pre-training may also be performed again after the pre-training from the spatial view is performed and then the data from the environmental view is excluded. Excluding the influence from the environmental view refers to that the pre-training sample may not carry the data of the environment semantic feature.

In step S130, the pre-trained air quality prediction model is trained by adopting a formal training sample and a formal training objective function.

Based on the air quality prediction model after the pre-training, the formal training is performed by adopting the formal training sample including complete data, so that the air quality prediction model can converge more quickly and the training process can be completed. The pre-training sample and the pre-training objective function are different from the formal training sample and the formal training objective function, so the air quality prediction model can be trained from different scales and views. Optionally, the air quality prediction model in the present disclosure predicts air quality from multiple views such as the spatial view, the temporal view and the environmental view. Due to many factors considered, the model needs vast computing cost. Therefore, one time of pre-training or two times of pre-training one after another may be firstly performed on one or two set factors, and then on the basis of the pre-trained model, then the overall formal training is performed on the model. In this way, it is convenient for the model to converge quickly, and the computing cost is reduced.

According to the technical solution of the embodiment of the present disclosure, the air quality of fine-grained regions is predicted from multiple views such as the spatial view, the temporal view and the environmental view, so that the prediction of air quality can be more accurate and refined. At the same time, the mode of pre-training is adopted, so that the computing cost of model training is reduced and the convergence is quick.

Figure 2:
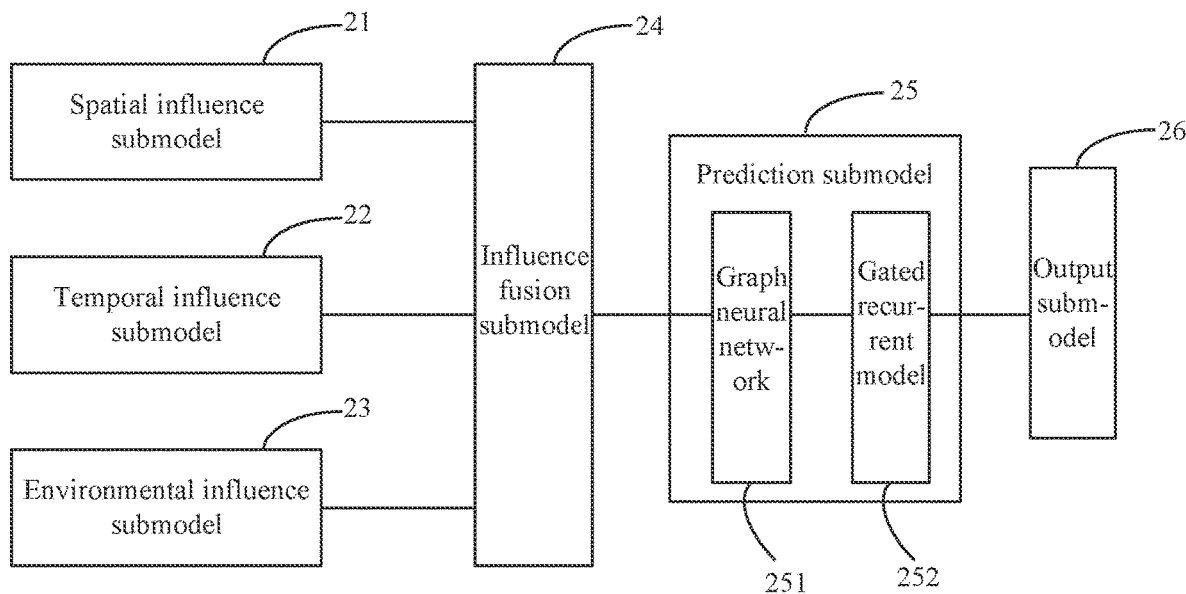
FIG. 2 is a diagram showing an architecture of an air quality prediction model according to an embodiment of the present disclosure.

FIG. 2 is a diagram showing an architecture of an air quality prediction model according to an embodiment of the present disclosure. The embodiment provides a preferred model architecture based on the preceding embodiment.

As shown in FIG. 2, the air quality prediction model includes: a spatial influence submodel 21, a temporal influence submodel 22, an environmental influence submodel 23, an influence fusion submodel 24, a prediction submodel 25 and an output submodel 26.

An output terminal of the spatial influence submodel 21, an output terminal of the temporal influence submodel 22 and an output terminal of the environmental influence submodel 25 are respectively connected to the influence fusion submodel 24, and the influence fusion submodel 24 is configured to perform, based on a self-attention layer, key information extraction and fusion on quality vectors respectively output by the spatial influence submodel 21, the temporal influence submodel 22 and the environmental influence submodel 23 and output a fusion quality vector.

The prediction submodel 25 is configured to calculate and output a predicted quality vector at a future occasion according to the influence fusion submodel 24. Optionally, the prediction submodel 25 includes a graph neural network 251 and a gated recurrent model 252. The graph neural network 251 is configured to perform updating on the fusion quality vector according to spatial influence between each region to output a graph quality vector, where each region is configured as a node in the graph, a graph quality vector of the each region is configured as an attribute of the node, and air quality spatial influence between adjacent regions is configured as an edge weight value of the node. The gated recurrent model 252 is configured to calculate and output a predicted quality vector at a future occasion according to graph quality vectors of a region at least two historical occasions.

The output submodel 26 is configured to generate an air quality predicted value of a region according to the prediction submodel 25 based on a feedforward neural network.

The air quality prediction model provided by the embodiment can separately consider the spatial influence, the temporal influence and the environmental influence based on the spatial influence submodel 21, the temporal influence submodel 22, and the environmental influence submodel 23 of multiple views, and calculate and obtain the air quality vector of the prediction regions based on limited air quality measurement values of the measurement regions. The prediction submodel 25 includes the graph neural network 251 and the gated recurrent model 252, so that the spatial influence between regions can be considered through the graph neural network in the prediction link, and the temporal influence of the air quality of the regions can also be considered through the gated recurrent model, and more accurate prediction results can be obtained.

Among the above solutions, the preferred solutions are described below.

The spatial influence submodel 21 is configured to calculate and output a spatial quality vector of the prediction regions based on the air quality measurement values of the measurement regions according to the spatial influence between the each region.

The temporal influence submodel 22 is a gated recurrent model and is configured to calculate and output a temporal quality vector at a current occasion according to air quality measurement values of the measurement regions at least two historical occasions.

The environmental influence submodel 23 is configured to aggregate air quality measurement values of the measurement regions who have a set environment semantic similarity with the prediction regions and obtain an aggregated environmental quality vector.

The above-mentioned quality vectors, such as the spatial quality vector, the temporal quality vector, the environmental quality vector, the fusion quality vector and the graph quality vector, are all characterization vectors of the air quality of the regions, and are quality vectors output by a certain submodel as intermediate data. The measurement values are generally scalar values of some indicators, and the quality vectors are features of the scalar values of the air quality of the regions. The vector data expressed in the form of vectors is more suitable for calculation in the deep learning model.

After fusion of the air quality vector from multiple views, in the process of air quality prediction based on the prediction submodel, the spatial influence of the air quality of the regions can be considered through the graph neural network, and the temporal influence can be considered based on the gated recurrent model, so that effective prediction of air quality at a future occasion is performed. In both of the prediction submodel and the temporal influence submodel, the gated recurrent model is used to consider the influence of the air quality at different occasions in the regions, and the law of the temporal influence is consistent. Therefore, the prediction submodel and the temporal influence submodel can reuse the same gated recurrent model. In this way, after the temporal influence submodel learns temporal influence model parameters at a current occasion of the regions through training, the temporal influence model parameters can be reused to the influence of air quality at each occasion of the regions during the prediction stage.

The output submodel, as an output layer of the air quality prediction model, can output the predicted value of the air quality in the form of a scalar, which is convenient for users to identify.

The air quality prediction model provided in the embodiment includes models operating at two stages. At the first stage, the spatial influence submodel, the temporal influence submodel and the environmental influence submodel can consider, from multiple views, the influence on the air quality of the regions at a current occasion from adjacent regions, historical occasions and regions of the similar environment, so as to calculate the air quality vector of each prediction region at the current occasion and each historical occasion. The second stage is the prediction stage, which can predict the air quality at a future occasion based on the air quality vector of each region at each occasion calculated and obtained in the first stage. The final prediction result may be output in the form of a scalar through the output submodel who is configured as an output layer. The overall model architecture is a multi-view and multi-task architecture, which can accurately predict fine-grained air quality of regions.

The following separately introduces the optional implementation solutions of each submodel of the air quality prediction model in the embodiment of the present disclosure.

First, regarding the spatial influence submodel, the spatial influence submodel considers the influence between regions from a spatial view and infers the air quality of the current uncovered regions (that is, the prediction regions) from the spatial view. Specifically, the goal is to learn and obtain the air quality vector of the prediction regions based on the adjacent measurement regions with air quality measurement values.

Optionally, the spatial influence submodel satisfies a following formula:

$$x_i^d = \Sigma_{j \in N_s} s_{ij} W_s x_j^a.$$

$x_i^d$ denotes the spatial quality vector output by the spatial influence submodel, that is, the spatial quality vector of the prediction regions, $R_l$ denotes a set of all prediction regions and satisfies that $r_i \in R_l$, $W_s$ denotes a to-be-trained parameter matrix, which is a to-be-learned parameter matrix shared by all regions, $N_s$ denotes a set of measurement regions satisfying a set proximity condition of a prediction region $r_i$, $r_j \in N_s$. For example, the set proximity condition is that measurement regions are located within a set distance from the prediction regions, such as measurement regions located within the range of 10 km to 20 km from the prediction regions. $x_j^a$ denotes air quality measurement values of a measurement region $r_j$, and $s_{ij}$ denotes a weight of a distance between the regions and satisfies a following formula:

$$s_{ij} = \exp\left(-\frac{dist(r_i, r_j)}{\delta^2}\right).$$

$dist(r_i, r_j)$ denotes a geospatial distance between the region $r_i$ and the region $r_j$, and $\delta$ represents a standard deviation of the distance.

Through the above spatial influence submodel, the spatial distance between the regions is considered, and then the relative relationship between the air quality measurement values of the measurement regions and the air quality vector of the prediction regions is determined through learning. Therefore, the air quality vector of adjacent regions can be calculated and obtained effectively based on the limited measurement values.

Second, regarding the temporal influence submodel, the temporal influence submodel considers the air quality vector of the regions from the temporal view. Specifically, local temporal information can be infused through a gated recurrent network, and air quality can be further inferred from the temporal view. The gated recurrent network, also referred to as the gated recurrent model, is a simple and effective variant of the recurrent neural network. The gated recurrent network can consider the influence of the air quality of a region at multiple historical occasions on the air quality at a current occasion, and model the long-term dependence of the time sequence. The gated recurrent model includes a hidden layer and can output a hidden layer vector H. The hidden layer vector H can reflect the features of the input air quality vector.

Optionally, the temporal influence submodel satisfies a following formula:

$$x_i^{e,t} = W_t h_i^{t-1}.$$

$x_i^{e,t}$ denotes a temporal quality vector output by the temporal influence submodel at an occasion t, $h_i^{t-1}$ denotes a hidden layer output vector of the temporal influence submodel at an occasion t−1, and $h_i^{t-1}$ is calculated as follows:

$$h_i^{t-1} = (1 - z_i^{t-1}) \cdot h_i^{t-2} + z_i^{t-1} \cdot \tilde{h}_i^{t-1}.$$

$z_i^{t-1}$ satisfies a formula $z_i^{t-1} = \sigma(W_z[h_i^{t-2}, x_i^{e,t-1}] + b_z)$, $r_i^{t-1}$ satisfies a formula $r_i^{t-1} = \sigma(W_r[h_i^{t-2}, x_i^{e,t-1}] + b_r)$, and $\tilde{h}_i^{t-1}$ satisfies a formula $\tilde{h}_i^{t-1} = \tanh(Wh[r_i^{t-1} \cdot h_i^{t-2}, x_i^{e,t-2}] + b_{\tilde{h}})$.

$W_t$, $W_z$, $W_r$, and $W_r$ denote to-be-translated parameter matrices, $b_z$, $b_r$, and $b_{\tilde{h}}$ are to-be-translated parameters, and · is a position multiplying symbol.

The spatial quality vector of each region at the occasion t−1 is output by the spatial influence submodule, the hidden layer state $h_i^{t-1}$ at the occasion t−1 can be calculated by the above formula, and $h_i^{t-1}$ contains the air quality information before the occasion t, so that the temporal quality vector $x_i^{e,t}$ at the occasion t from the temporal view can be obtained.

Through the temporal influence submodel, the continuity of the air quality changing over time in the regions can be effectively considered, so that the prediction accuracy of air quality is higher.

Third, regarding the environmental influence submodel, the environmental influence submodel learns the air quality relationship of the regions from the environmental view. The principle is that regions with the similar environment have similar air quality features. The environment is characterized by an environment semantic feature, also referred to as the environmental context, which can reflect the static environmental factors that affect the air quality of a region, such as a green belt, an industrial region, an administrative region, or a road network set in the region, and all of these factors affect the air quality. In practice, environmental factors in regions of a city may use points of interest (POI) and road network density to reflect the environment semantic feature. Specifically, the environment semantic feature includes an environmental influence category and/or road network data of the points of interest covered within the region. Points of interest may be classified according to the environmental influence category. The specific environmental influence category may be preset according to requirements, such as including an excellent level, a good level, a moderate level and a poor level. The environmental influence category of a green belt is the excellent level, and the environmental influence category of a chemical plant is the poor level. The road network data may further be included and is reflected by the number of road sections and the density of road sections. The environment semantic feature may be constructed as a vector, and each element in the vector reflects the environmental influence category and the road network data of the POI, which can be spliced together to form the environment semantic feature, so that the environmental factors of the region can be accurately reflect.

Further, an environment semantic similarity between regions can be determined based on the environment semantic feature, and then through an environment semantic aggregator, the air quality measurement values of the measurement regions with the similar environment semantic feature are aggregated to calculate the air quality vector of the prediction regions, which is recorded as the environmental quality vector.

Optionally, the environmental influence submodel satisfies a following formula:

$$x_i^s = \Sigma_{j \in N_c} c_{ij} W_e x_j^a.$$

$x_i^s$ denotes an environmental quality vector output by an environmental influence submodel of a prediction region $r_i$, $x_j^a$ denotes air quality measurement values of measurement regions $r_j$, $W_e$ denotes a to-be-trained parameter matrix, $N_c$ denotes a set of measurement regions satisfying a set environment semantic similarity with the prediction regions $r_i$, and $c_{ij}$ denotes an environment semantic similarity of the region $r_i$ and the region $r_j$ and satisfies a following formula:

$$c_{ij} = \exp(-sim(x_i^c, x_j^c)).$$

sim(·,·) is a similarity function based on Euclidean distance, and $x_i^c$ and $x_j^c$ respectively denote environment semantic features of the region $r_i$ and the region $r_j$.

The air quality relationship between regions is considered from the environmental view, so that the measurement values of the measurement regions can be effectively used to calculate the predicted value of the region with the similar environment.

After the spatial influence submodel, the temporal influence submodel and the environmental influence submodel are respectively constructed, the spatial quality vector, the temporal quality vector and the environmental quality vector of each region at the occasion t as output can be obtained. Then, the spatial quality vector $x_i^d$, the temporal quality vector $x_i^{e,t}$ and the environmental quality vector $x_i^s$ are fused. In the embodiment of the present disclosure, $x_i^d$, $x_i^{e,t}$, and $x_i^s$ can be directly averaged for fusion, but it is preferable to introduce a self-attention layer to adaptively extract relevant important information from the above-mentioned quality vector.

Optionally, the influence fusion submodel satisfies a following formula:

$$x_i^u = \alpha_i^d x_i^d + \alpha_i^e x_i^{e,t} + \alpha_i^s x_i^s.$$

$x_i^u$ denotes an air quality vector output by the influence fusion submodel, $x_i^d$ denotes an air quality vector output by a spatial influence submodel of a region $r_i$, $x_i^{e,t}$ denotes an air quality vector output by a temporal influence submodel of the region $r_i$ at an occasion t, $x_i^s$ denotes an air quality vector output by the environmental influence submodel, a superscript k∈{d, e, s}, superscripts d, e, s respectively represent quality vectors output by the spatial influence submodel, the temporal influence submodel and the environmental influence submodel, and $\alpha_i^k$ is determined according to a following formula:

$$\alpha_i^k = \frac{Attn(x_i^k, x_i^m, x_i^c)}{\sum_k Attn(x_i^k, x_i^m, x_i^c)}.$$

Attn(•) is an attention mechanism function, and $x_i^m$ and $x_i^c$ respectively denote a weather feature and an environment semantic feature of the region $r_i$.

Based on the above spatial influence submodel, the temporal influence submodel and the environmental influence submodel, the air quality vector of each region at the occasion t can be determined based on limited measurement values to predict the air quality data at future occasions (an occasion t+1, an occasion t+2 and so on), and the calculation may be specifically performed through the prediction submodel.

For the air quality prediction of a region at a future occasion, the spatial influence of adjacent regions, the temporal influence of the same region, and the environmental influence of the region will also be considered.

For the spatial influence, the graph neural network is used to learn the air quality influence relationship between regions. First, each region is configured as a node, and a topology graph is constructed. Each region is configured as a node in the graph, a graph quality vector of the each region is configured as an attribute of the node, and air quality spatial influence between adjacent regions is configured as an edge weight value of the node. The initial graph quality vector of the graph may adopt a fusion quality vector output by the influence fusion submodel. Then, the fusion quality vector is adjusted through the learning of the graph neural network.

Optionally, the graph neural network satisfies a following formula:

$$X^t = GConv(X^u, A_R) = \sigma\left(D^{-\frac{1}{2}} A_R D^{-\frac{1}{2}} X^u W\right).$$

$X^t$ denotes a matrix of a graph quality vector updated through a graph convolution operation GConv ( ), $X^u$ denotes a matrix of the fusion quality vector, D denotes a degree matrix of nodes (each element of the degree matrix reflects the number of neighbor nodes in the region corresponding to the position at which the element is located), σ is a nonlinear activation function, W denotes a to-be-trained parameter matrix, and $A_R$ denotes an adjacency matrix, may adopt Gaussian Kernel, and is calculated by a following formula:

$$a_{ij}^r = \exp\left(-\frac{dist(v_i, v_j)^2}{\delta^2}\right).$$

$v_i$ and $v_j$ respectively denote region center points of a region $r_i$ and a region $r_j$, $dist(v_i, v_j)$ is used to calculate a geospatial distance between the region center points, δ denotes a standard deviation of the distance, and $a_{ij}^r$ denotes a matrix element in the adjacency matrix and represents an edge weight of an adjacent region node.

The graph neural network is adopted, so that the spatial correlation of regions can be reflected, the air quality vector of the regions can be adjusted during the prediction process, and the accuracy of the prediction is improved.

The air quality of each region is not only correlated to adjacent nodes on the graph, but also affected by the air quality at a previous occasion. Therefore, a gated recurrent unit (GRU) is introduced to the prediction submodel. The graph neural network is infused into the gated recurrent model for temporal dependence modeling. Considering the region $r_i$ and the air quality vector $((x_i^{t-T}, x_i^{t-T+}, \ldots x_i^t))$ of the region $r_i$ at past T occasions, $x_i^t$ that satisfies $x_i^t \in X^t$ is the output of the graph convolution operation at an occasion t. Since $x_i^t$ contains the spatial correlation information at the occasion t, and $h_i^{t-1}$ contains the temporal and spatial correlation information before the occasion t, so that the obtained $h_i^t$ will contain both the temporal and spatial correlation information. The hidden layer state $h_i^t$ of the GRU simultaneously encodes the past temporal and spatial dependence information and can thus be directly used for air quality prediction of the regions. The prediction submodel may reuse the gated recurrent model of the temporal influence submodel.

The output of the prediction submodel is the air quality vector. In order to better express the air quality value, it is optional to output through the output submodel. For example, the output submodel adopts a feedforward neural network f(•) to output the air quality predicted value, and the output submodel satisfies a following formula:

$$(\hat{y}_i^{t+1}, \hat{y}_i^{t+2}, \ldots, \hat{y}_i^{t+\tau}) = f(h_i^t, x_i^w, x_i^c).$$

$x_i^w$ and $x_i^c$ respectively denote a weather forecast feature and an environment semantic feature of a region $r_i$, and $h_i^t$ denotes a hidden layer output vector of a gated recurrent model of the prediction submodel. Therefore, air quality predicted values $\hat{y}_i^{t+1}, \hat{y}_i^{t+2}, \ldots, \hat{y}_i^{t+\tau}$ from an occasion t+1 to an occasion t+τ can be predicted and obtained.

The output submodel adopted in the embodiment of the present disclosure combines the hidden layer output vector in the prediction submodel and combines the environment semantic feature and a weather situation feature, so that various situations can be comprehensively considered, and the prediction results can be more accurate. The hidden layer output vector of the prediction submodel fully reflects the features of the spatial influence, the temporal influence and the environmental influence on the air quality of the regions.

In the embodiment of the present disclosure, the air quality prediction model is pre-trained through at least one time of pre-training. The pre-training adopted in the embodiment of the present disclosure may include node-level pre-training and task-level pre-training, and then formal training is performed. The pre-training process is described in detail below through embodiments.

First, regarding the node-level pre-training, the goal of the node-level pre-training is to learn a general-purpose graph neural network (GNN) to encode the topological attributes of various graphs. The main idea of the node-level pre-training is to use topological information as a supervisory signal to optimize characterization of a region and make adjacent regions close to each other in latent space. Specifically, a fusion quality vector $x_i^u$ of a region $r_i$ obtained in multi-view and multi-task learning is adopted, then a special-purpose GNN is trained, and a context quality vector $x_i^{cx}$ is obtained by aggregating and transforming the characterization $x_j$ of the adjacent regions satisfying that $x_j \in N_i$. The goal of a node-level pre-training task is to optimize the cosine similarity between quality vectors and the context quality vector of the current region.

Specifically, during the node-level pre-training, the pre-training sample is air quality measurement values of each measurement region at least two historical occasions, and the pre-training objective function is a similarity between graph quality vectors of the regions.

Optionally, a cosine similarity $L_p$ denotes the similarity between the graph quality vectors of the regions, and satisfies a formula as follows:

$$L_p = -\log(\sigma(x_i^T x_i^{cx})) - E_{j \in P_n(i)}[\log(\sigma(-x_i^T x_j^{cx}))].$$

$\sigma$ is a nonlinear activation function, $P_n(i)$ denotes a set of negative sampling distribution regions of a region $r_i$, $x_i^T$ and $x_j^T$ respectively denote transpositions of a graph quality vector of the region $r_i$ and a graph quality vector of a region $r_j$, $x_i^{cx}$ and $x_j^{cx}$ respectively denote an aggregated vector of graph quality vectors of an adjacent region of the region $r_i$ and an aggregated vector of graph quality vectors of an adjacent region of the region $r_j$, and E is a function for calculating an average value.

The initial value of the graph quality vector is the fusion quality vector, which is updated to the graph quality vector after processing on the graph neural network. The set of negative sampling distribution regions is a set of regions randomly determined from adjacent regions of any region.

The node-level pre-training can consider from the view of the spatial influence of the region, and the model can be pre-trained with a relatively small calculation scale, so that the convergence speed of the model can be improved, and the calculation cost can be reduced.

Second, regarding the task-level pre-training, on the basis of the node-level pre-training, the task-level pre-training may be further introduced. Various features of the regions are adopted as supervision signals, and the knowledge of highly correlated prediction tasks is infused into model parameters. Generally speaking, any feature of the regions can be used as a self-supervised signal. However, in practical applications, the granularity of meteorological features is relatively rough (that is, some adjacent nodes may share the same meteorological information), and the environment semantic feature (such as the POI and the road network) do not change over time. As a result, predicting these features with less information may introduce additional noise and cause negative transfer. For this reason, during the task-level pre-training, only air quality features of the regions are used as self-supervised signals. Specifically, only regions provided with monitoring stations are used to construct a region graph, and each node on the graph has real air quality measurement values. A GNN is trained to extract air quality information and environmental information around each node, and spatial correlation is modeled. Then, a fully connected layer is used to process the output of the GNN, and a final air quality predicted value of each node is obtained. The model further fine-tunes the GNN obtained in the node-level pre-training under self-supervised learning. The task-level pre-training follows a multi-task learning paradigm of hard-parameter sharing, so that different supervision signals can be backpropagated through the output layer of a specific task. Pre-trained network parameters integrate general-purpose graph topology information and various environment semantic information. These network parameters are applied to future downstream fine-grained air quality prediction tasks and are fine-tuned.

Specifically, during the task-level pre-training, the pre-training sample may be air quality measurement values of each measurement region at least two historical occasions, and the pre-training objective function is a mean squared error function between an air quality predicted value output by the air quality prediction model and an air quality measurement value.

It can be seen from the above introduction that the task-level pre-training can simplify the module training process by excluding the participation of the environment semantic feature.

In general, a spatiotemporal pre-training strategy can separately adopt the node-level pre-training or the task-level pre-training. Preferably, the node-level pre-training is performed first, and then the task-level pre-training is performed.

In the embodiment of the present disclosure, the operation of pre-training the air quality prediction model by adopting the pre-training sample and the pre-training objective function, optionally, includes the steps described below.

Node-level pre-training is performed on the air quality prediction model by adopting air quality measurement values of each measurement region at least two historical occasions as the pre-training sample and configuring a similarity between graph quality vectors of the regions as a node pre-training objective function.

Task-level pre-training is performed on the air quality prediction model by adopting air quality measurement values of each measurement region at least two historical occasions as the pre-training sample and adopting a mean squared error function between an air quality predicted value output by the air quality prediction model and air quality measurement values as a task pre-training objective function.

Through the joint training of the node-level pre-training and the task-level pre-training, the spatial influence of the air quality of the region can be optimized first, and then the temporal influence can be further optimized, while the difficulty of training is reduced and the calculation is speeded up.

After the pre-training, in the embodiment of the present disclosure, formal training is performed based on the pre-trained air quality prediction model. For the model after the pre-training, model parameters have been optimized to a certain extent, and the model can converge more quickly during the formal training process.

For the formal training, optionally, the formal training sample includes air quality measurement values of each measurement region at least two historical occasions and an environment semantic feature of a region. The formal training objective function includes a first formal objective function and a second formal objective function, where the first formal objective function is a function of a classification result of the fusion quality vector output by the influence fusion submodel, and the second formal objective function is a least square error between a minimized air quality measurement value and an air quality predicted value.

During the formal training, the training sample includes comprehensive features, that is, measurement values of each measurement region at each occasion, as well as the environment semantic feature of each region. The formal training objective function preferably includes two parts. The first formal objective function focuses on determining the classification result of the influence fusion sub-model, that is, determining whether the calculation of the air quality vector of the region is accurate out of the prediction link. The second formal objective function supervises and learns the relationship between the predicted value and the measurement value of the sample from the perspective of the final predicted value, thereby optimizing the model.

The following introduces the optional implementation of the first formal objective function and the second formal objective function.

Optionally, the first formal objective function includes a mean squared error function for an air quality numerical regression task and all occasions, and a cross-entropy loss function for an air quality index classification task. An Adam optimizer may be used to train the entire model.

Specifically, a following formula may be adopted as the first formal objective function $L_1$:

$$L_1 = \beta_1 L_r + \beta_2 L_c.$$

$\beta_1$ and $\beta_2$ respectively denote hyperparameters controlling importance of the air quality numerical regression task and the index classification task.

$L_r$ is the mean squared error function for the air quality numerical regression task and the all occasions, and satisfies a following formula:

$$L_r = -\frac{1}{T|R_1|}\sum_{i=1}^{|R_1|}\sum_{t=1}^{T}(\hat{y}_i^{r,t} - y_i^{r,t})^2.$$

$L_c$ is the cross-entropy loss function for the air quality index classification task, and satisfies a following formula:

$$L_c = -\frac{1}{T|R_1|}\sum_{i=1}^{|R_1|}\sum_{t=1}^{T}\sum_{t=1}^{T} y_i^{c,t}\log\hat{y}_i^{c,t}.$$

T denotes a set of occasions involved in a training sample, t denotes a serial number of the occasions, $R_1$ denotes a set of all of measurement regions, $\hat{y}_i^{r,t}$ denotes an air quality predicted value of a region $r_i$ at an occasion t, and $y_i^{r,t}$ donates air quality measurement values of the region $r_i$ at the occasion t.

$$\hat{y}_i^c = \text{Softmax}(w_c x_i^u).$$

$\hat{y}_i^{r,t}$ represents an air quality distribution category of the region $r_i$, $y_i^{c,t}$ denotes an air quality distribution category of the region $r_i$ at the occasion t, $W_c$ denotes a to-be-trained parameter matrix, and $x_i^u$ denotes the fusion quality vector.

In the embodiment of present disclosure, in order to make the air quality numerical prediction result more stable, a multi-category classification task is further introduced to infer the current air quality index, and the task is defined as $\hat{y}_i^c$ representing the predicted air quality distribution category of the region $r_i$. The distribution category is calculated by discretizing the air quality index (AQI) value. Several category intervals may be set according to requirements for a discretization interval, such as category 1: 0 to 50, category 2: 50 to 100, category 3: 100 to 150, category 4: 150 to 200, category 5: 200 to 300, and category 6: 300 to 500. When the air quality index value of a certain region is 160, the value belongs to the category 4 after discretization. The category is further encoded by one-hot into a one-dimensional vector, such as [0, 0, 0, 1, 0, 0], which is used as the distribution category.

The cross-entropy loss function for the air quality index classification task is used to classify the result reflecting the air quality vector of the region which affects output the fusion submodel, and use the classification result to perform correcting training on the model to make the model training more accurate.

The air quality numerical regression task is to convert the air quality vector in the form of a vector and reflecting the features of the air quality of the region into an air quality value in the form of a scalar of the region through a regression method, and to perform optimization on the model based on the scalar value, so as to avoid errors introduced in the subsequent output process of the vector and the scalar.

Optionally, the air quality predicted value is calculated and determined by adopting a linear regression unit that satisfies a following formula:

$$\hat{y}_i^r = w_r X_i^u.$$

$\hat{y}_i^{t+j}$ denotes an air quality predicted value of the region $r_i$, and $w_r$ denotes a to-be-trained parameter matrix.

Specifically, a following formula may be adopted as the second formal objective function:

$$L_2 = \frac{1}{\tau|R|}\sum_{i=1}^{|R|}\sum_{j=1}^{\tau}(\hat{y}_i^{t+j} - y_i^{t+j})^2.$$

$\hat{y}_i^{t+j}$ denotes an air quality predicted value of a region $r_i$ output by the output submodel at an occasion t+1, and $y_i^{t+j}$ denotes an air quality measurement value of the region $r_i$ at the occasion t+1.

The second formal objective function further considers the overall output results of the prediction submodel and the output submodel, and comprehensively performs feedback optimization training on the entire model.

The technical solutions of the embodiment of the present disclosure do not need to rely on accurate pollution source information, and thus will not cause serious deviations in air quality prediction due to insufficient pollution source information. Moreover, fine-grained air quality prediction can be achieved. Predicting the air quality of fine-grained regions is very beneficial to people's travel decisions and government policy making. Especially, for the environment prediction in regions with relatively few infrastructures, the demand for fine-grained prediction is particularly urgent.

In the embodiment of the present disclosure, the air quality forecast at a region level is configured as a semi-supervised deep learning problem. First, a multi-view and multi-task learning framework is used to estimate the air quality of the regions not covered by monitoring stations, and then a graph convolutional network and a gated recurrent network are used to model the spatial correlation and the temporal correlation of the regions, and the final prediction results are generated. The performance of the deep neural network relies heavily on a large amount of labeled data. However, due to the sparseness of air quality data of the regions, tag information cannot be fully utilized, which may lead to unsatisfactory prediction results. Therefore, a spatiotemporal pre-training strategy is proposed to learn robust and transferable neural network parameters, so that the model can be easily fine-tuned for downstream tasks with only a few tags. In the embodiment of the present disclosure, the key of the spatiotemporal pre-training strategy is to use graph topology and environmental context information to perform self-supervised learning. Specifically, the spatiotemporal pre-training includes two parts: node-level pre-training and task-level pre-training.

The technical solution of the embodiment of the present disclosure uses sparse historical air quality measurement data, weather data and environment semantic data of regions to propose a real-time air quality prediction model based on multi-view and multi-task learning, fuses different views and assists air quality index classification tasks, so that the prediction performance of the model is improved.

The above technical solutions overcome the limitations of the value-based method, and learn air quality modes directly from a large amount of historical data without relying on specific pollution source information.

Related technical solutions and products are mainly based on a station level or a city level to predict air quality, while the embodiment of the present disclosure performs more refined modeling and perform fine-grained air quality prediction on streets and township-level regions, so as to provide better decision support for local governments and people's travel. Through the spatiotemporal pre-training strategy, the information of regions can be utilized more efficiently, more robust and transferable model parameters can be learned, and the generalization performance of the air quality prediction can be improved.

Figure 3:
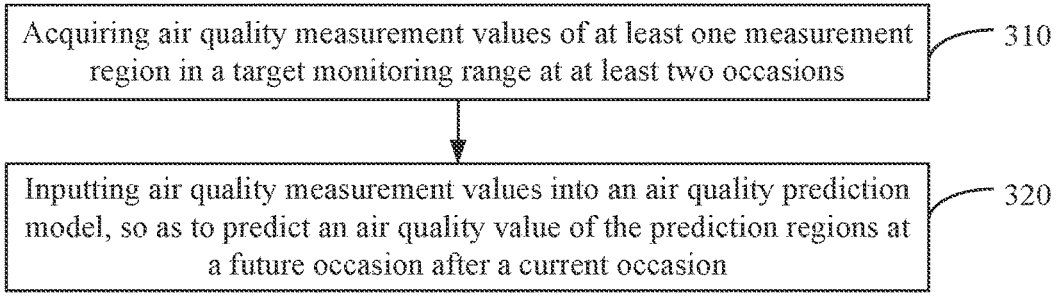
FIG. 3 is a flowchart of an air quality prediction method according to an embodiment of the present disclosure.

FIG. 3 is a flowchart of an air quality prediction method according to an embodiment of the present disclosure. The method is used for predicting air quality, and may be executed by an air quality prediction apparatus. The apparatus may be implemented by software and/or hardware and configured in an electronic device. Preferably, the method may be implemented as an air quality prediction function in a client, such as a weather forecast client. The method includes the steps described below.

In step S310, air quality measurement values of at least one measurement region in a target monitoring range at least two occasions are acquired, where the target monitoring range is divided into multiple regions, and the multiple regions include measurement regions with air quality measurement values and prediction regions without the air quality measurement values.

In step S320, the air quality measurement values are input into an air quality prediction model, so as to predict an air quality value of the prediction regions at a future occasion after a current occasion.

The air quality prediction model is trained by the training method for an air quality prediction model provided by the embodiment of the present disclosure.

The technical solution of the embodiment of the present disclosure solves the problem during fine-grained air quality prediction. For example, a city may be divided into non-overlapped regions according to streets and towns. Based on sparse measurement data from air quality monitoring stations and multi-source heterogeneous city data, the future air quality of each region is predicted. Through the technical solution of the embodiment of the present disclosure, the air quality of each region of the city can be accurately predicted in advance, and potential loss caused by air pollution can be reduced or even prevented through pollution emission control and early intervention. In this way, the future air quality of regions that are not covered by monitoring stations can be effectively predicted.

Figure 4:
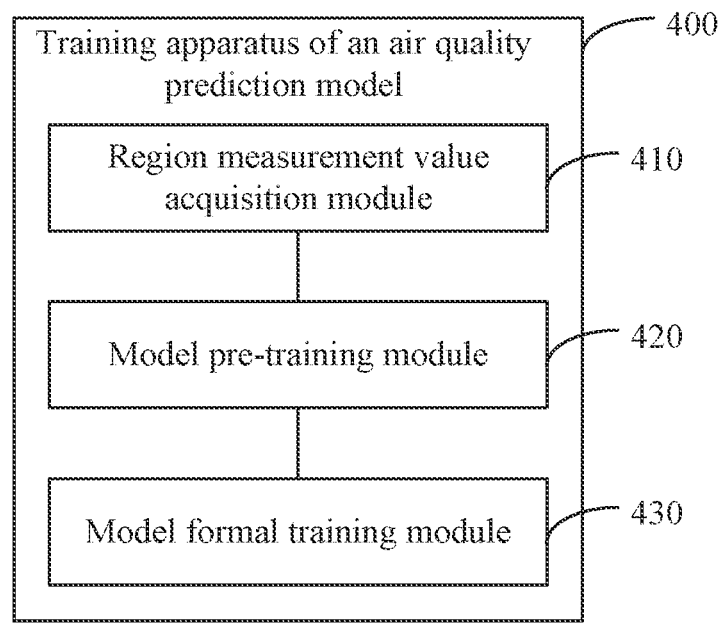
FIG. 4 is a structural block diagram of a training apparatus of an air quality prediction model according to an embodiment of the present disclosure.

FIG. 4 is a structural block diagram of a training apparatus of an air quality prediction model according to an embodiment of the present disclosure. The apparatus 400 includes a region measurement value acquisition module 410, a model pre-training module 420 and a model formal training module 430.

The region measurement value acquisition module 410 is configured to divide a target monitoring range into multiple regions, where the multiple regions include measurement regions with air quality measurement values and prediction regions without the air quality measurement values, and to acquire the air quality measurement values in the measurement regions.

The model pre-training module 420 is configured to pre-train the air quality prediction model by adopting a pre-training sample and a pre-training objective function, where the pre-training sample includes the measurement values.

The model formal training module 430 is configured to train the pre-trained air quality prediction model by adopting a formal training sample and a formal training objective function, where the formal training sample includes the measurement values. The air quality prediction model is configured to predict air quality of the multiple regions according to spatial information, historical information and environmental information.

Optionally, the apparatus is set as described below.

The air quality prediction model includes: a spatial influence submodel, a temporal influence submodel, an environmental influence submodel, an influence fusion submodel, a prediction submodel, and an output submodel.

An output terminal of the spatial influence submodel, an output terminal of the temporal influence submodel, and an output terminal of the environmental influence submodel are respectively connected to the influence fusion submodel, and the influence fusion submodel is configured to perform key information extraction and fusion on quality vectors respectively output by the spatial influence submodel, the temporal influence submodel, and the environmental influence submodel based on a self-attention layer and output a fusion quality vector.

The prediction submodel is configured to calculate and output a predicted quality vector at a future occasion according to the influence fusion submodel.

The output submodel is configured to generate an air quality predicted value of a region according to the prediction submodel based on a feedforward neural network.

Optionally, the apparatus is set as described below.

The prediction submodel includes a graph neural network and a gated recurrent model.

The graph neural network is configured to perform updating on the fusion quality vector according to spatial influence between each region to output a graph quality vector, where each region is configured as a node in the graph, a graph quality vector of the each region is configured as an attribute of the node, and air quality spatial influence between adjacent regions is configured as an edge weight value of the node; and the gated recurrent model is configured to calculate and output a predicted quality vector at a future occasion according to graph quality vectors at least two historical occasions of a region.

Optionally, the apparatus is set as described below.

The spatial influence submodel is configured to calculate and output a spatial quality vector of the prediction regions based on the air quality measurement values of the measurement regions according to the spatial influence between the each region.

The temporal influence submodel is a gated recurrent model and is configured to calculate and output a temporal quality vector at a current occasion according to air quality measurement values of the measurement regions at least two historical occasions.

The environmental influence submodel is configured to aggregate air quality measurement values of the measurement regions who have a set environment semantic similarity with the prediction regions and obtain an aggregated environmental quality vector.

Optionally, the apparatus is set as described below.

The prediction submodel and the temporal influence submodel reuse a gated recurrent model.

Optionally, the apparatus is set as described below.

The pre-training sample is air quality measurement values of each measurement region at least two historical occasions, and the pre-training objective function is a similarity between graph quality vectors of the regions.

Optionally, the apparatus is set as described below.

A cosine similarity $L_s$ denotes the similarity between the graph quality vectors of the regions, and satisfies a formula as follows:

$$L_p = -\log(\sigma(x_i^T x_i^{cx})) - E_{j \in P_n(i)}[\log((-x_i^T x_j^{cx}))].$$

$\sigma$ is a nonlinear activation function, $P_n(i)$ denotes a set of negative sampling distribution regions of a region $r_i$, $x_i^T$ and $x_j^T$ respectively denotes transpositions of a graph quality vector of the region $r_i$ and a graph quality vector of a region $r_j$, $x_i^{cx}$ and $x_j^{cx}$ respectively denote an aggregated vector of graph quality vectors of an adjacent region of the region $r_i$ and an aggregated vector of graph quality vectors of an adjacent region of the region $r_j$, and $E$ is a function for calculating an average value.

Optionally, the apparatus is set as described below.

The pre-training sample is air quality measurement values of each measurement region at least two historical occasions, and the pre-training objective function is a mean squared error function between an air quality predicted value output by the air quality prediction model and an air quality measurement value.

Optionally, the apparatus is set as described below.

The model pre-training module specifically includes a node-level pre-training unit and a task-level pre-training unit.

The node-level pre-training unit is configured to perform node-level pre-training on the air quality prediction model by adopting air quality measurement values of each measurement region at least two historical occasions as the pre-training sample and configuring a similarity between graph quality vectors of the regions as a node pre-training objective function.

The task-level pre-training unit is configured to perform task-level pre-training on the air quality prediction model by adopting air quality measurement values of each measurement region at least two historical occasions as the pre-training sample and adopting a mean squared error function between an air quality predicted value output by the air quality prediction model and air quality measurement values as a task-level pre-training objective function.

Optionally, the apparatus is set as described below.

The formal training sample includes air quality measurement values of each measurement region at least two historical occasions and an environment semantic feature of a region. The formal training objective function includes a first formal objective function and a second formal objective function, where the first formal objective function is a function of a classification result of the fusion quality vector output by the influence fusion submodel, and the second formal objective function is a least square error between a minimized air quality measurement value and an air quality predicted value.

Optionally, the apparatus is set as described below.

The first formal objective function includes a mean squared error function for an air quality numerical regression task and all occasions, and a cross-entropy loss function for an air quality index classification task.

Optionally, the apparatus is set as described below.

The first formal objective function $L_1$ satisfies a following formula:

$$L_1 = \beta_1 L_r + \beta_2 L_c.$$

$\beta_1$ and $\beta_2$ respectively denote hyperparameters controlling importance of the air quality numerical regression task and the index classification task.

$L_r$ is the mean squared error function for the air quality numerical regression task and the all occasions, and satisfies a following formula:

$$L_r = \frac{1}{\tau|R_l|} \sum_{i=1}^{|R_l|} \sum_{t=1}^{T} (\hat{y}_i^{r,t} - y_i^{r,t})^2.$$

$L_c$ is the cross-entropy loss function for the air quality index classification task, and satisfies a following formula:

$$L_c = -\frac{1}{T|R_l|} \sum_{i=1}^{|R_l|} \sum_{t=1}^{T} \sum_{t=1}^{T} y_i^{c,t} \log \hat{y}_i^{c,t}.$$

T denotes a set of occasions involved in a training sample, t denotes a serial number of the occasions, $R_l$ denotes a set of all of measurement regions, $\hat{y}_i^{r,t}$ denotes an air quality predicted value of a region $r_i$ at an occasion t, and $y_i^{r,t}$ denotes air quality measurement values of the region $r_i$ at the occasion t.

$$\hat{y}_i^c = \text{Softmax}(w_c x_i^u).$$

$\hat{y}_i^c$ represents an air quality distribution category of the region $r_i$, $y_i^{c,t}$ denotes an air quality distribution category of the region $r_i$ at the occasion t, $W_c$ denotes a to-be-trained parameter matrix, and $x_i^u$ denotes the fusion quality vector.

Optionally, the apparatus is set as described below.

The air quality predicted value is calculated and determined by adopting a linear regression unit that satisfies a following formula:

$$\hat{y}_i^r = W_r x_i^u.$$

$\hat{y}_i^{t+j}$ denotes an air quality predicted value of the region $r_i$, and $w_r$ denotes a to-be-trained parameter matrix.

Optionally, the apparatus is set as described below.

The second formal objective function satisfies a following formula:

$$L_2 = \frac{1}{\tau|R|} \sum_{i=1}^{|R|} \sum_{j=1}^{\tau} (\hat{y}_i^{t+j} - y_i^{t+j})^2.$$

$\hat{y}_i^{t+j}$ denotes an air quality predicted value of a region $r_i$ output by the output submodel at an occasion t+1, and $y_i^{t+j}$ denotes an air quality measurement value of the region $r_i$ at the occasion t+1.

Optionally, the apparatus is set as described below.

The spatial influence submodel satisfies a following formula:

$$x_i^d = \sum_{j \in N_s} s_{ij} W_s x_j^a.$$

$x_i^d$ denotes the spatial quality vector output by the spatial influence submodel, $R_l$ denotes a set of all of prediction regions, $r_i \in R_l$, $W_s$ denotes a to-be-trained parameter matrix, $N_s$ denotes a set of measurement regions satisfying a set proximity condition of a prediction regions $r_i$, $r_j \in N_s$, $x_j^a$ denotes an air quality measurement value of a measurement region $r_j$, and $s_{ij}$ denotes a weight of a distance between the regions and satisfies a following formula:

$$s_{ij} = \exp\left(-\frac{dist(r_i, r_j)}{\delta^2}\right).$$

$dist(r_i, r_j)$ denotes a geospatial distance between the region $r_i$ and the region $r_j$, and $\delta$ represents a standard deviation of the distance.

Optionally, the apparatus is set as described below. The temporal influence submodel satisfies a following formula:

$$x_i^{e,t} = W_t h_i^{t-1}.$$

$x_i^{e,t}$ denotes a temporal quality vector output by the temporal influence submodel at an occasion t, $h_i^{t-1}$ denotes a hidden layer output vector of the temporal influence submodel at an occasion t−1, and $h_i^{t-1}$ is calculated as follows:

$$h_i^{t-1} = (1 - z_i^{t-1}) \cdot h_i^{t-2} + z_i^{t-1} \cdot \tilde{h}_i^{t-1}.$$

$z_i^{t-1}$ satisfies a formula $z_i^{t-1} = \sigma(W_z[h_i^{t-2}, x_i^{e,t-1}] + b_z)$, $r_i^{t-1}$ satisfies a formula $r_i^{t-1} = \sigma(W_r[h_i^{t-2}, x_i^{e,t-1}] + b_r)$, and $\tilde{h}_i^{t-1}$ satisfies a formula $\tilde{h}_i^{t-1} = \tanh(W_{\tilde{h}}[r_i^{t-1} \cdot h_i^{t-2}, x_i^{e,t-1}] + b_{\tilde{h}})$.

$W_t$, $W_z$, $W_r$, and $W_{\tilde{h}}$ denote to-be-translated parameter matrices, $b_z$, $b_r$, and $b_{\tilde{h}}$ are to-be-translated parameters, and · is a position multiplying symbol.

Optionally, the apparatus is set as described below. An environment semantic feature includes an environmental influence category and/or road network data of points of interest covered within a region.

Optionally, the apparatus is set as described below. The environmental influence submodel satisfies a following formula:

$$x_i^s = \sum_{j \in N_c} c_{ij} W_c x_j^a.$$

$x_i^s$ denotes an environmental quality vector output by an environmental influence submodel of a prediction region $r_i$, $x_j^a$ denotes air quality measurement values of a measurement region $r_j$, $W_c$ denotes a to-be-trained parameter matrix, $N_c$ denotes a set of measurement regions satisfying a set environment semantic similarity with the prediction regions $r_i$, $c_{ij}$ denotes an environment semantic similarity of the region $r_i$ and the region $r_j$ and satisfies a following formula:

$$c_{ij} = \exp(-sim(x_i^c, x_j^c)).$$

$sim(\cdot,\cdot)$ is a similarity function based on Euclidean distance, and $x_i^c$ and $x_j^c$ respectively are denote environment semantic features of the region $r_i$ and the region $r_j$.

Optionally, the apparatus is set as described below. The influence fusion submodel satisfies a following formula:

$$x_i^u + \alpha_i^d x_i^d + \alpha_i^e x_i^{e,t} + \alpha_i^s x_i^s.$$

$x_i^u$ denotes an air quality vector output by the influence fusion submodel, $x_i^d$ denotes an air quality vector output by a spatial influence submodel of a region $r_i$, $x_i^{e,t}$ denotes an air quality vector output by a temporal influence submodel of the region $r_i$ at an occasion t, $x_i^s$ denotes an air quality vector output by the environmental influence submodel, a superscript $k \in \{d, e, s\}$, superscripts d, e, s respectively represent quality vectors output by the spatial influence submodel, the temporal influence submodel, and the environmental influence submodel, and $\alpha_i^k$ is determined according to a following formula:

$$\alpha_i^k = \frac{Attn(x_i^k, x_i^m, x_i^c)}{\sum_k Attn(x_i^k, x_i^m, x_i^c)}.$$

$Attn(\cdot)$ is an attention mechanism function, and $x_i^m$ and $x_i^c$ respectively denote a weather feature and an environment semantic feature of the region $r_i$.

Optionally, the apparatus is set as described below. The graph neural network satisfies a following formula:

$$X^t = GConv(X^u, A_R) = \sigma\left(D^{-\frac{1}{2}} A_R D^{-\frac{1}{2}} X^u W\right).$$

$X^t$ denotes a matrix of a graph quality vector updated through a graph convolution operation $GConv(\ )$, $X^u$ denotes a matrix of the fusion quality vector, D denotes a degree matrix of nodes, $\sigma$ is a nonlinear activation function, W denotes a to-be-trained parameter matrix, and $A_R$ denotes an adjacency matrix and is calculated by a following formula:

$$a_{ij}^r = \exp\left(-\frac{dist(v_i, v_j)^2}{\delta^2}\right).$$

$v_i$ and $v_j$ respectively denote region center points of a region $r_i$ and a region $r_j$, $dist(v_i, v_j)$ is used to calculate a geospatial distance between the region center points, $\delta$ denotes a standard deviation of the distance, and $a_{ij}^r$ denotes a matrix element in the adjacency matrix and represents an edge weight of an adjacent region node.

Optionally, the apparatus is set as described below. The output submodel satisfies a following formula:

$$(\hat{y}_i^{t+1}, \hat{y}_i^{t-2}, \ldots, \hat{y}_i^{t-\tau}) = f(h_i^t, x_i^w, x_i^c)$$

$x_i^w$ and $x_i^c$ respectively denote a weather forecast feature and an environment semantic feature of a region $r_i$, and $h_i^t$ denotes a hidden layer output vector of a gated recurrent model.

Optionally, the apparatus is set as described below. The region measurement value acquisition module is configured to perform the step described below.

The target predicting range is divided into the multiple regions in units of road sections or streets.

Optionally, the apparatus is set as described below. The region measurement value acquisition module is configured to perform the steps described below.

Measurement values of one air quality monitoring station in the measurement regions are configured as the air quality measurement values of the measurement regions.

Alternatively, an average value of measurement values of multiple air quality monitoring stations in the measurement regions are calculated as the air quality measurement values of the measurement regions.

The training apparatus of an air quality prediction model provided by the embodiment of the present disclosure may be used to execute the training method for an air quality prediction model provided by the embodiment of the present disclosure, and has corresponding functions and modules.

Figure 5:
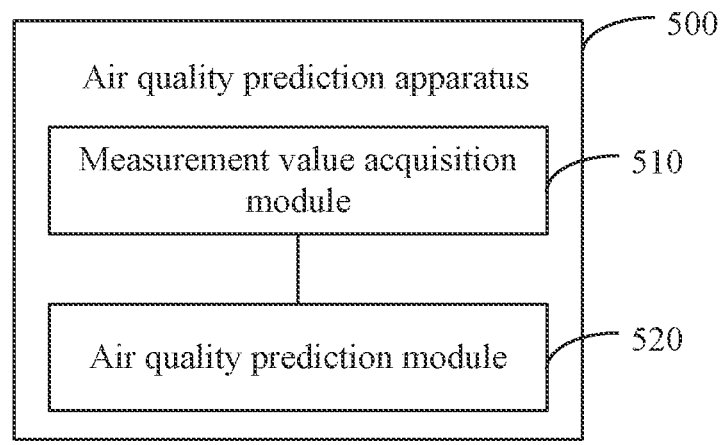
FIG. 5 is a structural block diagram of an air quality prediction apparatus according to an embodiment of the present disclosure.

FIG. 5 is a structural block diagram of an air quality prediction apparatus according to an embodiment of the present disclosure. The apparatus 500 includes a measurement value acquisition module 510 and an air quality prediction module 520.

The measurement value acquisition module 510 is configured to acquire air quality measurement values of at least one measurement region in a target monitoring range at least two occasions, where the target monitoring range is divided into multiple regions, and the multiple regions include measurement regions with air quality measurement values and prediction regions without the air quality measurement values.

The air quality prediction module 520 is configured to input the air quality measurement values into an air quality prediction model, so as to predict an air quality value of the prediction regions at a future occasion after a current occasion.

The air quality prediction model is trained by the training method for an air quality prediction model provided by any embodiment of the present disclosure.

The air quality prediction apparatus provided by the embodiment of the present disclosure may be used to execute the air quality prediction method provided by the embodiment of the present disclosure, and has corresponding functions and modules.

According to the embodiment of the present disclosure, the present disclosure further provides an electronic device, a readable storage medium and a computer program product.

Figure 6:
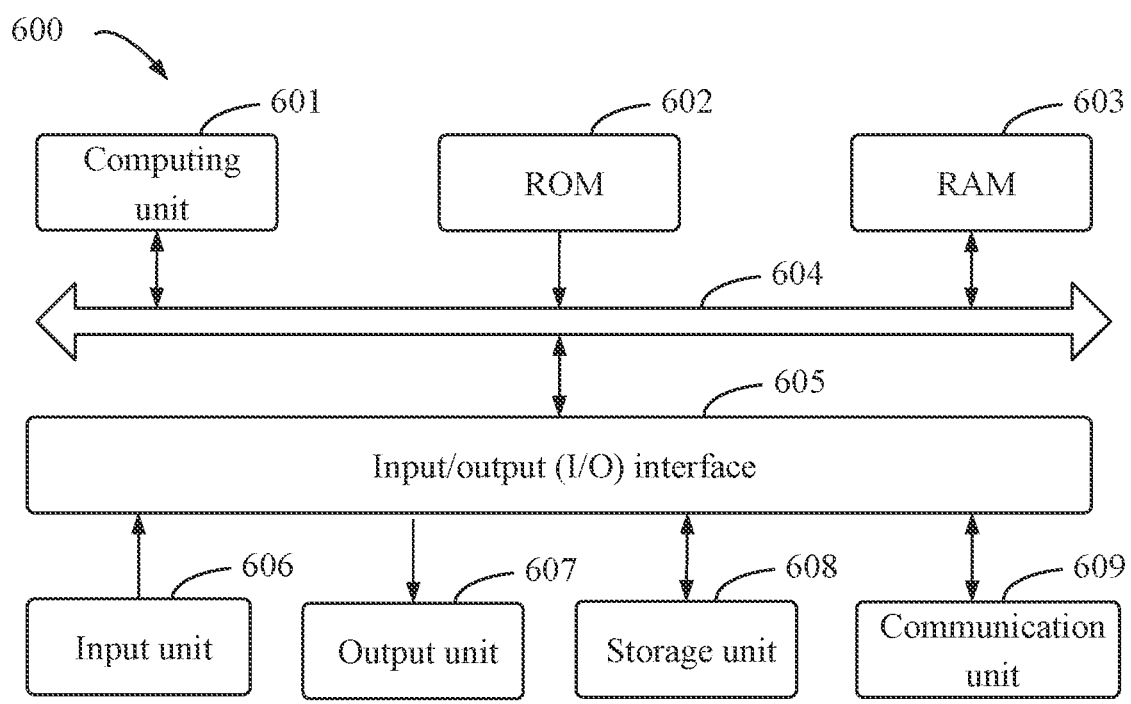
FIG. 6 is a schematic block diagram of an example electronic device for implementing the embodiments of the present disclosure.

FIG. 6 is a schematic block diagram of an example electronic device 600 for implementing the embodiments of the present disclosure. The electronic device 700 is intended to represent various forms of digital computers, for example, laptop computers, desktop computers, worktables, personal digital assistants, servers, blade servers, mainframe computers and other applicable computers. The electronic device may also represent various forms of mobile apparatus, for example, personal digital assistants, cellphones, smartphones, wearable devices and other similar computing apparatus. Herein the shown components, the connections and relationships between these components, and the functions of these components are illustrative only and are not intended to limit the implementation of the present disclosure as described and/or claimed herein.

As shown in FIG. 6, the device 600 includes a computing unit 601. The computing unit 601 may perform various types of appropriate operations and processing based on a computer program stored in a read-only memory (ROM) 602 or a computer program loaded from a storage unit 608 to a random-access memory (RAM) 603. The RAM 603 may also store various programs and data required for operations of the device 600. The computing unit 601, the ROM 602 and the RAM 603 are connected to each other by a bus 904. An input/output (I/O) interface 605 is also connected to the bus 604.

Multiple components in the electronic device 600 are connected to the I/O interface 605. The multiple components include an input unit 606 such as a keyboard and a mouse, an output unit 607 such as various types of displays and speakers, the storage unit 608 such as a magnetic disk and an optical disk, and a communication unit 609 such as a network card, a modem and a wireless communication transceiver. The communication unit 609 allows the device 600 to exchange information/data with other devices over a computer network such as the Internet and/or over various telecommunication networks.

The computing unit 601 may be a general-purpose and/or special-purpose processing component having processing and computing capabilities. Examples of the computing unit 601 include, but are not limited to, a central processing unit (CPU), a graphics processing unit (GPU), a special-purpose artificial intelligence (AI) computing chip, a computing unit executing machine learning model algorithms, a digital signal processor (DSP), and any appropriate processor, controller and microcontroller. The computing unit 601 performs various preceding methods and processing, such as the training method for an air quality prediction model or the air quality prediction method. For example, in some embodiments, the training method for an air quality prediction model or the air quality prediction method may be implemented as a computer software program tangibly contained in a machine-readable medium, for example, the storage unit 608. In some embodiments, part or all of computer programs may be loaded and/or installed on the device 600 via the ROM 602 and/or the communication unit 609. When the computer program is loaded to the RAM 603 and executed by the computing unit 601, one or more steps of the training method for an air quality prediction model or the air quality prediction method may be executed. Alternatively, in other embodiments, the computing unit 601 may be configured to execute the training method for an air quality prediction model or the air quality prediction method in any other appropriate manner (for example, by use of firmware).

The preceding various embodiments of systems and techniques may be implemented in digital electronic circuitry, integrated circuitry, a field-programmable gate array (FPGA), an application-specific integrated circuit (ASIC), an application-specific standard product (ASSP), a system on a chip (SoC), a complex programmable logic device (CPLD), computer hardware, firmware, software and/or any combination thereof. The various embodiments may include implementations in one or more computer programs. The one or more computer programs are executable and/or interpretable on a programmable system including at least one programmable processor. The programmable processor may be a special-purpose or general-purpose programmable processor for receiving data and instructions from a storage system, at least one input apparatus and at least one output apparatus and transmitting the data and instructions to the storage system, the at least one input apparatus and the at least one output apparatus.

Program codes for implementation of the method of the present disclosure may be written in any combination of one or more programming languages. These program codes may be provided for the processor or controller of a general-purpose computer, a special-purpose computer or another programmable data processing apparatus to enable functions/operations specified in a flowchart and/or a block diagram to be implemented when the program codes are executed by the processor or controller. The program codes may all be executed on a machine; may be partially executed on a machine; may serve as a separate software package that is partially executed on a machine and partially executed on a remote machine; or may all be executed on a remote machine or a server.

In the context of the present disclosure, the machine-readable medium may be a tangible medium that contains or stores a program available for an instruction execution system, apparatus or device or a program used in conjunction with an instruction execution system, apparatus or device. The machine-readable medium may include, but is not limited to, an electronic, magnetic, optical, electromagnetic, infrared or semiconductor system, apparatus or device, or any appropriate combination thereof. Concrete examples of the machine-readable storage medium may include an electrical connection based on one or more wires, a portable computer disk, a hard disk, a random-access memory (RAM), a read-only memory (ROM), an erasable programmable read-only memory (EPROM) or a flash memory, an optical fiber, a portable compact disc read-only memory (CD-ROM), an optical storage device, a magnetic storage device, or any appropriate combination thereof.

In order that interaction with a user is provided, the systems and techniques described herein may be implemented on a computer. The computer has a display apparatus (for example, a cathode-ray tube (CRT) or liquid-crystal display (LCD) monitor) for displaying information to the user; and a keyboard and a pointing apparatus (for example, a mouse or a trackball) through which the user can provide input to the computer. Other types of apparatus may also be used for providing interaction with a user. For example, feedback provided for the user may be sensory feedback in any form (for example, visual feedback, auditory feedback or haptic feedback). Moreover, input from the user may be received in any form (including acoustic input, voice input or haptic input).

The systems and techniques described herein may be implemented in a computing system including a back-end component (for example, a data server), a computing system including a middleware component (for example, an application server), a computing system including a front-end component (for example, a client computer having a graphical user interface or a web browser through which a user can interact with implementations of the systems and techniques described herein) or a computing system including any combination of such back-end, middleware or front-end components. The components of the system may be interconnected by any form or medium of digital data communication (for example, a communication network). Examples of the communication network include a local area network (LAN), a wide area network (WAN), a blockchain network and the Internet.

The computing system may include clients and servers. A client and a server are generally remote from each other and typically interact through a communication network. The relationship between the client and the server arises by virtue of computer programs running on the respective computers and having a client-server relationship to each other. The server may be a cloud server, also referred to as a cloud computing server or a cloud host. As a host product in a cloud computing service system, the server solves the defects of difficult management and weak service scalability in a related physical host and a related VPS service.

It is to be understood that various forms of the preceding flows may be used, with steps reordered, added or removed. For example, the steps described in the present disclosure may be executed in parallel, in sequence or in a different order as long as the desired result of the technical solution disclosed in the present disclosure is achieved. The execution sequence of these steps is not limited herein.

The scope of the present disclosure is not limited to the preceding embodiments. It is to be understood by those skilled in the art that various modifications, combinations, subcombinations and substitutions may be made according to design requirements and other factors. Any modifications, equivalent substitutions, improvements and the like made within the spirit and principle of the present disclosure are within the scope of the present disclosure.

It is to be understood that various forms of the preceding flows may be used, with steps reordered, added or removed. For example, the steps described in the present disclosure may be executed in parallel, in sequence or in a different order as long as the desired result of the technical solution disclosed in the present disclosure is achieved. The execution sequence of these steps is not limited herein.

The scope of the present disclosure is not limited to the preceding embodiments. It is to be understood by those skilled in the art that various modifications, combinations, subcombinations and substitutions may be made according to design requirements and other factors. Any modifications, equivalent substitutions, improvements and the like made within the spirit and principle of the present disclosure are within the scope of the present disclosure.

What is claimed is:

1. A training method for an air quality prediction model, comprising:
    dividing a target monitoring range into a plurality of regions, wherein the plurality of regions comprise measurement regions with air quality measurement values and prediction regions without the air quality measurement values, and acquiring the air quality measurement values in the measurement regions;
    pre-training the air quality prediction model by adopting a pre-training sample and a pre-training objective function, wherein the pre-training sample comprises the measurement values; and
    training the pre-trained air quality prediction model by adopting a formal training sample and a formal training objective function, wherein the formal training sample comprises the measurement values;
    wherein the air quality prediction model is configured to predict air quality of the plurality of regions according to spatial information, historical information and environmental information;
    wherein the air quality prediction model comprises: a spatial influence submodel, a temporal influence submodel, an environmental influence submodel, an influence fusion submodel, a prediction submodel, and an output submodel; wherein
    an output terminal of the spatial influence submodel, an output terminal of the temporal influence submodel and an output terminal of the environmental influence submodel are respectively connected to the influence fusion submodel, and the influence fusion submodel is configured to perform, based on a self-attention layer, key information extraction and fusion on quality vectors respectively output by the spatial influence submodel, the temporal influence submodel and the environmental influence submodel and output a fusion quality vector;
    the prediction submodel is configured to calculate and output a predicted quality vector at a future occasion according to the influence fusion submodel; and
    the output submodel is configured to generate an air quality predicted value of a region according to the prediction submodel based on a feedforward neural network;
    wherein the prediction submodel comprises a graph neural network and a gated recurrent model; and wherein the graph neural network is configured to perform updating on the fusion quality vector according to spatial influence between each of the plurality of regions to output a graph quality vector, wherein each of the plurality of regions is configured as a node in the graph, a graph quality vector of the each of the plurality of regions is configured as an attribute of the node, and air quality spatial influence between adjacent regions among the plurality of regions is configured as an edge weight value of the node; and the gated recurrent model is configured to calculate and output a predicted quality vector at a future occasion according to graph quality vectors of a region at least two historical occasions.

2. The method according to claim 1, wherein
the spatial influence submodel is configured to calculate and output a spatial quality vector of the prediction regions based on the air quality measurement values of the measurement regions according to the spatial influence between the each of the plurality of regions;
the temporal influence submodel is the gated recurrent model and is configured to calculate and output a temporal quality vector at a current occasion according to air quality measurement values of the measurement regions at least two historical occasions; and
the environmental influence submodel is configured to aggregate air quality measurement values of the measurement regions who have a set environment semantic similarity with the prediction regions and obtain an aggregated environmental quality vector.

3. The method according to claim 2, wherein the prediction submodel and the temporal influence submodel reuse a gated recurrent model.

4. The method according to claim 1, wherein the pre-training sample is air quality measurement values of each of the measurement regions at least two historical occasions, and the pre-training objective function is a similarity between graph quality vectors of the plurality of regions.

5. The method according to claim 1, wherein the pre-training sample is air quality measurement values of each of the measurement regions at least two historical occasions, and the pre-training objective function is a mean squared error function between an air quality predicted value output by the air quality prediction model and an air quality measurement value.

6. The method according to claim 1, wherein the pre-training the air quality prediction model by adopting the pre-training sample and the pre-training objective function comprises:
performing node-level pre-training on the air quality prediction model by adopting air quality measurement values of each of the measurement regions at least two historical occasions as the pre-training sample and configuring a similarity between graph quality vectors of the plurality of regions as a node pre-training objective function; and
performing task-level pre-training on the air quality prediction model by adopting air quality measurement values of each of the measurement regions at least two historical occasions as the pre-training sample and adopting a mean squared error function between an air quality predicted value output by the air quality prediction model and an air quality measurement value as a task pre-training objective function.

7. The method according to claim 1, wherein the formal training sample comprises air quality measurement values of each of the measurement regions at least two historical occasions and an environment semantic feature of a region; and
the formal training objective function comprises a first formal objective function and a second formal objective function, wherein the first formal objective function is a function of a classification result of the fusion quality vector output by the influence fusion submodel, and the second formal objective function is a least square error between a minimized air quality measurement value and an air quality predicted value.

8. The method according to claim 2, wherein the spatial influence submodel satisfies a following formula:

$$x_i^d = \Sigma_{j \in N_s} s_{ij} W_s x_j^a,$$

wherein $x_i^d$ denotes the spatial quality vector output by the spatial influence submodel, $R_i$ denotes a set of all prediction regions and satisfies that $r_i \in R_i$, $W_s$ denotes a to-be-trained parameter matrix, $N_s$ denotes a set of measurement regions satisfying a preset proximity condition of a prediction region $r_i$, a number of the measurement regions in the set of the measurement regions is greater than 2, $r_j \in N_s$, $x_j^a$ denotes air quality measurement values of a measurement region $r_j$, and $s_{ij}$ denotes a weight of a distance between the plurality of regions and satisfies a following formula:

$$s_{ij} = \exp\left(-\frac{dist(r_i, r_j)}{\delta^2}\right),$$

wherein $dist(r_i, r_j)$ denotes a geospatial distance between the region $r_i$ and the region $r_j$, and $\delta$ represents a standard deviation off all geospatial distances.

9. The method according to claim 2, wherein the temporal influence submodel satisfies a following formula:

$$x_i^{e,t} = W_t h_i^{t-1},$$

wherein $x_i^{e,t}$ denotes a temporal quality vector output by the temporal influence submodel at an occasion t, $h_i^{t-1}$ denotes a hidden layer output vector of the temporal influence submodel at an occasion t−1, and $h_i^{t-1}$ is calculated as follows:

$$h_i^{t-1} = (1-z_i^{t-1}) \cdot h_i^{t-2} + z_i^{t-1} \cdot \tilde{h}_i^{t-1},$$

wherein $z_i^{t-1}$ satisfies a formula $z_i^{t-1} = \sigma(W_z[h_i^{t-2}, x_i^{e,t-1}] + b_z)$, $r_i^{t-1}$ satisfies a formula $r_i^{t-1} = \sigma(W_r[h_i^{t-2}, x_i^{e,t-1}] + b_r)$, and $\tilde{h}_i^{t-1}$ satisfies a formula $\tilde{h}_i^{t-1} = \tanh(W_{\tilde{h}}[r_i^{t-1} \cdot h_i^{t-2}, x_i^{e,t-1}] + b_{\tilde{h}})$, wherein $W_t$, $W_z$, $W_r$, and denote to-be-translated parameter matrices, $b_z$, $b_r$, $b_{\tilde{h}}$ are to-be-translated parameters, · is a position multiplying symbol, and $\sigma$ is a nonlinear activation function.

10. The method according to claim 2, wherein an environment semantic feature comprises an environmental influence category and/or road network data of points of interest covered within a region.

11. The method according to claim 2, wherein the environmental influence submodel satisfies a following formula:

$$x_i^s = \Sigma_{j \in N_c} c_{ij} W_c x_j^a,$$

wherein $x_i^s$ denotes an environmental quality vector output by an environmental influence submodel of a prediction region $r_i$, $x_j^a$ denotes air quality measurement values of measurement regions $r_j$, $W_c$ denotes a to-be-trained parameter matrix, $N_c$ denotes a set of measurement regions satisfying a set environment semantic similarity with the prediction regions $r_i$, and $c_{ij}$ denotes an environment semantic similarity of the region $r_i$ and the region $r_j$ and satisfies a following formula:

$$c_{ij} = \exp(-sim(x_i^c, x_j^c)),$$

wherein $sim(\cdot, \cdot)$ is a similarity function based on Euclidean distance; $x_i^c$ and $x_j^c$ respectively denote environment semantic features of the region $r_i$ and the region $r_j$, and exp ( ) is a Gaussian kernel function.

12. The method according to claim 2, wherein the influence fusion submodel satisfies a following formula:

$$x_i^u + \alpha_i^d x_i^d + \alpha_i^e x_i^{e,t} + \alpha_i^s x_i^s,$$

wherein $x_i^u$ denotes an air quality vector output by the influence fusion submodel, $x_i^d$ denotes an air quality vector output by a spatial influence submodel of a region $r_i$, $x_i^{e,t}$ denotes an air quality vector output by a temporal influence submodel of the region $r_i$ at an occasion t, $x_i^s$ denotes an air quality vector output by the environmental influence submodel, a superscript $k \in \{d, e, s\}$, superscripts d, e, s respectively represent quality vectors output by the spatial influence submodel, the temporal influence submodel and the environmental influence submodel, and $\alpha_i^k$ is determined according to a following formula:

$$\alpha_i^k = \frac{Attn(x_i^k, x_i^m, x_i^c)}{\sum_k Attn(x_i^k, x_i^m, x_i^c)},$$

wherein $Attn(\bullet)$ is an attention mechanism function, and $x_i^m$ and $x_i^c$ respectively denote a weather feature and an environment semantic feature of the region $r_i$.

13. The method according to claim 1, wherein the output submodel satisfies a following formula:

$$(\hat{y}_i^{t+1}, \hat{y}_i^{t-2}, \ldots, \hat{y}_i^{t-\tau}) = f(h_i^t, x_i^w, x_i^c)$$

wherein $x_i^w$ and $x_i^c$ respectively denote a weather forecast feature and an environment semantic feature of a region $r_i$, $h_i^t$ denotes a hidden layer output vector of a gated recurrent model, and $\hat{y}_i^{t+\tau}$ denote an air quality predicted value of a region $r_i$ at an occasion $t+\tau$.

14. The method according to claim 1, wherein the dividing the target monitoring range into the plurality of regions comprises:
dividing the target monitoring range into the plurality of regions in units of road sections or streets.

15. The method according to claim 1, wherein the acquiring the air quality measurement values in the measurement regions comprises:
configuring measurement values of one air quality monitoring station in the measurement regions as the air quality measurement values of the measurement regions; or
calculating an average value of measurement values of a plurality of air quality monitoring stations in the measurement regions as the air quality measurement values of the measurement regions.

16. An air quality prediction method, comprising:
acquiring air quality measurement values of at least one measurement region in a target monitoring range at least two occasions;
wherein the target monitoring range is divided into a plurality of regions, and the plurality of regions comprise measurement regions with air quality measurement values and prediction regions without the air quality measurement values; and
inputting the air quality measurement values into an air quality prediction model, so as to predict an air quality value of the prediction regions at a future occasion after a current occasion;
wherein the air quality prediction model is trained by the training method for an air quality prediction model according to claim 1.

17. An electronic device, comprising:
at least one processor; and
a memory communicatively connected to the at least one processor;
wherein the memory stores instructions executable by the at least one processor, and the instructions are executed by the at least one processor to cause the at least one processor to execute a training method for an air quality prediction model, wherein the training method comprises:
dividing a target monitoring range into a plurality of regions, wherein the plurality of regions comprise measurement regions with air quality measurement values and prediction regions without the air quality measurement values, and acquiring the air quality measurement values in the measurement regions;
pre-training the air quality prediction model by adopting a pre-training sample and a pre-training objective function, wherein the pre-training sample comprises the measurement values; and
training the pre-trained air quality prediction model by adopting a formal training sample and a formal training objective function, wherein the formal training sample comprises the measurement values;
wherein the air quality prediction model is configured to predict air quality of the plurality of regions according to spatial information, historical information and environmental information;
wherein the air quality prediction model comprises: a spatial influence submodel, a temporal influence submodel, an environmental influence submodel, an influence fusion submodel, a prediction submodel, and an output submodel; wherein
an output terminal of the spatial influence submodel, an output terminal of the temporal influence submodel and an output terminal of the environmental influence submodel are respectively connected to the influence fusion submodel, and the influence fusion submodel is configured to perform, based on a self-attention layer, key information extraction and fusion on quality vectors respectively output by the spatial influence submodel, the temporal influence submodel and the environmental influence submodel and output a fusion quality vector;
the prediction submodel is configured to calculate and output a predicted quality vector at a future occasion according to the influence fusion submodel; and
the output submodel is configured to generate an air quality predicted value of a region according to the prediction submodel based on a feedforward neural network;
wherein the prediction submodel comprises a graph neural network and a gated recurrent model; and wherein the graph neural network is configured to perform updating on the fusion quality vector according to spatial influence between each of the plurality of regions to output a graph quality vector, wherein each of the plurality of regions is configured as a node in the graph, a graph quality vector of the each of the plurality of regions is configured as an attribute of the node, and air quality spatial influence between adjacent regions among the plurality of regions is configured as an edge weight value of the node; and the gated recurrent model is configured to calculate and output a predicted quality vector at a future occasion according to graph quality vectors of a region at least two historical occasions.

18. A non-transitory computer-readable storage medium storing computer instructions for causing a computer to execute a training method for an air quality prediction model, wherein the training method comprises:

dividing a target monitoring range into a plurality of regions, wherein the plurality of regions comprise measurement regions with air quality measurement values and prediction regions without the air quality measurement values, and acquiring the air quality measurement values in the measurement regions;

pre-training the air quality prediction model by adopting a pre-training sample and a pre-training objective function, wherein the pre-training sample comprises the measurement values; and training the pre-trained air quality prediction model by adopting a formal training sample and a formal training objective function, wherein the formal training sample comprises the measurement values;

wherein the air quality prediction model is configured to predict air quality of the plurality of regions according to spatial information, historical information and environmental information;

wherein the air quality prediction model comprises: a spatial influence submodel, a temporal influence submodel, an environmental influence submodel, an influence fusion submodel, a prediction submodel, and an output submodel; wherein an output terminal of the spatial influence submodel, an output terminal of the temporal influence submodel and an output terminal of the environmental influence submodel are respectively connected to the influence fusion submodel, and the influence fusion submodel is configured to perform, based on a self-attention layer, key information extraction and fusion on quality vectors respectively output by the spatial influence submodel, the temporal influence submodel and the environmental influence submodel and output a fusion quality vector;

the prediction submodel is configured to calculate and output a predicted quality vector at a future occasion according to the influence fusion submodel; and the output submodel is configured to generate an air quality predicted value of a region according to the prediction submodel based on a feedforward neural network;

wherein the prediction submodel comprises a graph neural network and a gated recurrent model; and wherein the graph neural network is configured to perform updating on the fusion quality vector according to spatial influence between each of the plurality of regions to output a graph quality vector, wherein each of the plurality of regions is configured as a node in the graph, a graph quality vector of the each of the plurality of regions is configured as an attribute of the node, and air quality spatial influence between adjacent regions among the plurality of regions is configured as an edge weight value of the node; and the gated recurrent model is configured to calculate and output a predicted quality vector at a future occasion according to graph quality vectors of a region at least two historical occasions.

* * * * *